United States Patent [19]
Steg et al.

[11] Patent Number: 5,366,469
[45] Date of Patent: Nov. 22, 1994

[54] LANCET DEVICE FOR PUNCTURING THE SKIN

[75] Inventors: Hans-Henning Steg, Haninge; Helmut Seidl, Älvsjö, both of Sweden

[73] Assignee: Arta Plast AB, Tyresö, Sweden

[21] Appl. No.: 42,616

[22] Filed: Apr. 2, 1993

[30] Foreign Application Priority Data

Apr. 16, 1992 [DE] Germany ................ 4212723

[51] Int. Cl.⁵ ........................................ A61B 17/00
[52] U.S. Cl. ..................................................... 606/182
[58] Field of Search ........................... 606/181–185; 128/770, 667

[56] References Cited
U.S. PATENT DOCUMENTS

| | | | |
|---|---|---|---|
| 4,616,649 | 10/1986 | Burns | 606/182 |
| 5,026,388 | 6/1991 | Ingalz | 606/182 |
| 5,054,499 | 10/1991 | Swierczek | 606/182 |
| 5,201,324 | 4/1993 | Swierczek | 606/182 |

FOREIGN PATENT DOCUMENTS
3111737 2/1982 Germany.

*Primary Examiner*—Stephen C. Pellegrino
*Assistant Examiner*—William Lewis
*Attorney, Agent, or Firm*—Robert W. Becker & Associates

[57] ABSTRACT

A lancet device for puncturing the skin of mammals, especially humans, has a bushing with a grip portion and opposite the grip portion a free end defining a plane. An insert is axially slidably connected within the bushing. The insert has a first and a second end, with the first end having a grip element and the second end having a projecting lancet with a tip for puncturing the skin. The grip element comprises a diaphragm with a preset pressure point, and upon surpassing the pressure point of the diaphragm with an axially directed force in the direction toward the free end of the bushing, the lancet is released with a preset impulse via the insert and penetrates the plane defined by the free end to puncture the skin.

13 Claims, 3 Drawing Sheets

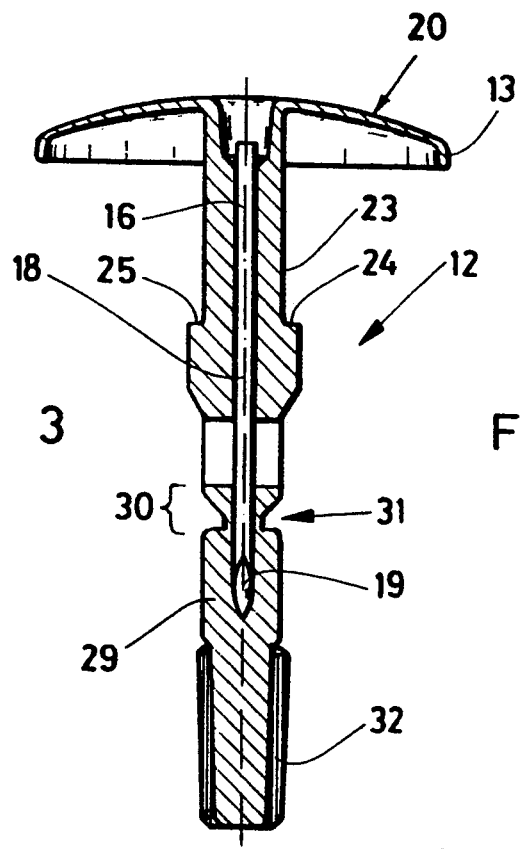
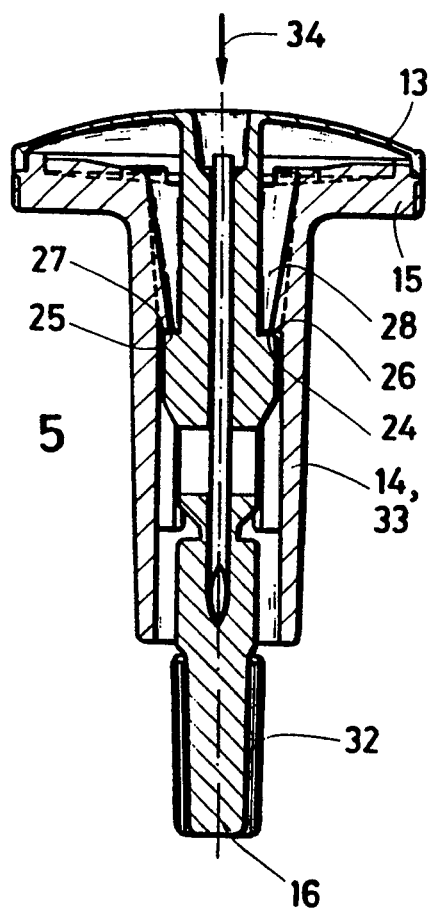
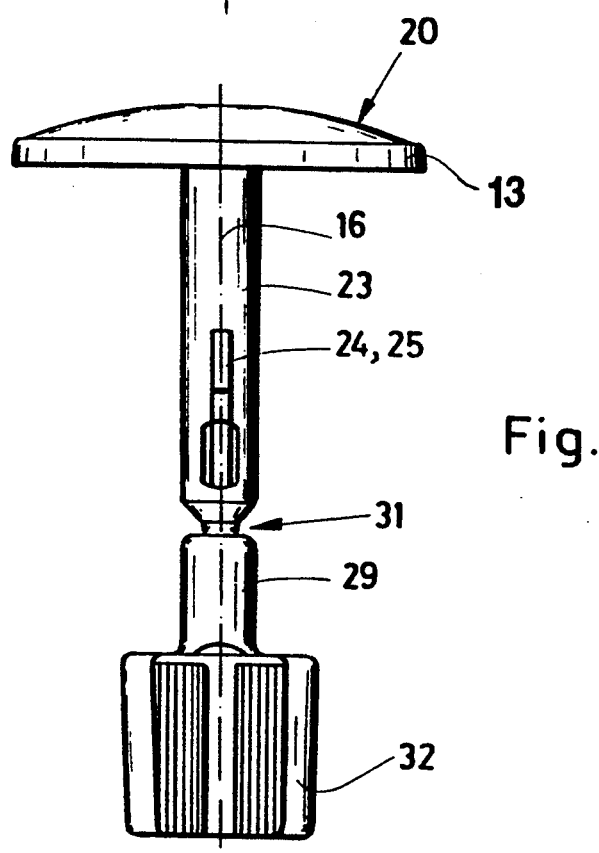

LANCET DEVICE FOR PUNCTURING THE SKIN

BACKGROUND OF THE INVENTION

The present invention relates to a lancet device for puncturing the skin of mammals, especially of humans, and comprises an insert with a grip element as well as a bushing with a grip portion, the bushing receiving the insert in an axially slidable manner, whereby the insert at its free end remote from the grip element is provided with a lancet having a tip for puncturing the skin.

Lancet devices for puncturing the skin, especially of humans, are known and are successfully being used in various embodiments in ambulatory facilities, in hospitals, in physicians practices, in red cross facilities as well as in emergency facilities, etc. in order to draw small amounts of blood for blood testing. An essential requirement for such lancet devices is that they must be producible at extremely low cost because they are used in great numbers in the aforementioned institutions and must be provided in great numbers at these facilities. A further essential requirement for these lancet devices that at least the portion of the lancet device that directly penetrates the skin of a human, i.e., that is directly in contact with the tissue beneath the skin and the blood stream of the human, must be maintained in sterile conditions until they are being used. In general, the portions of the lancet device which penetrate the tissue to a predetermined depth in order to connect with blood vessels for collecting the blood emerging from the penetration opening, are so-called lancets which have a substantially circular cross-section and are comprised of a steel body having a pointed end for puncturing the skin.

In general, such lancet device, after being used once for the designated puncturing function are not being reused because a subsequent sterilization of the lancet device is much more expensive than the manufacture of such a lancet device. Thus, the aforementioned lancet devices are usually single use devices.

From German Patent 31 11 737 a lancet device of the aforementioned kind is known. This lancet device is comprised of a bushing and an insert whereby the insert is provided with a lancet having a pointed end for the puncturing the skin at a free end of the insert remote from a corresponding grip element. The insert is provided with a radially extending peripheral bead portion which is arranged at the shaft-like insert at a predetermined distance to a pressure plate. The end of the insert remote from the peripheral bead portion which is also embodied as a shaft is arranged in the bushing which has an interior corresponding to the shaft cross-section of the insert. From the free end of the shaft of the insert the pointed end of the lancet projects. For performing the designated puncturing function with the known lancet device, the insert is in general axially displaced by the thumb of the operator via the grip element whereby the peripheral bead portion is pressed over corresponding radially inwardly extending bead provided at the interior of the bushing and projecting into the travel path of the insert; whereby the two beads are elastically deformed for overcoming their resistance relative to one another. After the resistance has been overcome the bead portion of the insert glides over the bead portion of the bushing and the lancet tip can puncture in the predetermined manner the skin, respectively, the tissue of the human, to a predetermined depth.

The known lancet device has substantial disadvantages. On the one hand, already during insertion of the insert element into the bushing the lancet tip can lose its sterility when, for example, the operator inserting the insert into bushing touches with the lancet tip the grip element at the inlet opening of the bushing element or touches his own skin. In summarizing the above, it can be said that during the introduction of the insert into the bushing a plurality of possibilities for desterilizing the lancet are present which is of special concern with respect to the treatment of HIV patients.

Even though in the known device the lancet tip is embedded within the material of the bushing, i.e., the insert and the bushing are manufactured in one step in the form of a single part by injection molding so that the sterility of the lancet tip in so far is completely guaranteed, in any case must the insert be removed from the bushing for the use of the lancet tip in order to be inserted into the bushing in the aforedescribed manner, whereby due to the required separation the lancet tip is freed and thus exposed to microbiological bacteria and viruses and other contaminants.

A further important disadvantage of the lancet device is that the release mechanism, depending on the manufacture and sensitivity of the operator using the lancet device is released with different velocities and thus applied with varying success so that the puncturing is not carried out in the required manner at all times, i.e., resulting in the required blood flow from the opening that has been made in the skin of the human.

It is furthermore disadvantageous that this known lancet device can only be manufactured in a very complicated and thus very costly process due to the absolute sterility requirements for at least the lancet tip.

It is therefore an object of the present invention to provide a lancet device of the aforementioned kind which is simple in its construction and thus less expensive to manufacture than the known lancet devices, which furthermore remains absolutely sterile until immediately before its use for puncturing the skin of a human, which consistently provides for a uniform puncturing function of the lancet tip for penetrating the skin of a human independent of the individual characteristics of the operator, and which furthermore after its use ensures that the lancet tip is protected so that no accidental injuries and resulting infections by the blood sticking to the lancet tip can occur.

BRIEF DESCRIPTION OF THE DRAWINGS

This object, and other objects and advantages of the present invention, will appear more clearly from the following specification in conjunction with the accompanying drawings, in which:

FIG. 3 shows a section of an insert with the cover element and grip at the free end of the insert;

FIG. 4 is a representation corresponding to FIG. 3 in a side view, but rotated about 90° about the insert axis relative to FIG. 3;

FIG. 5 is a lancet device according to the representation of FIG. 1 in cross-section, but rotated about the insert axis about 90°.

SUMMARY OF THE INVENTION

Figure 1:
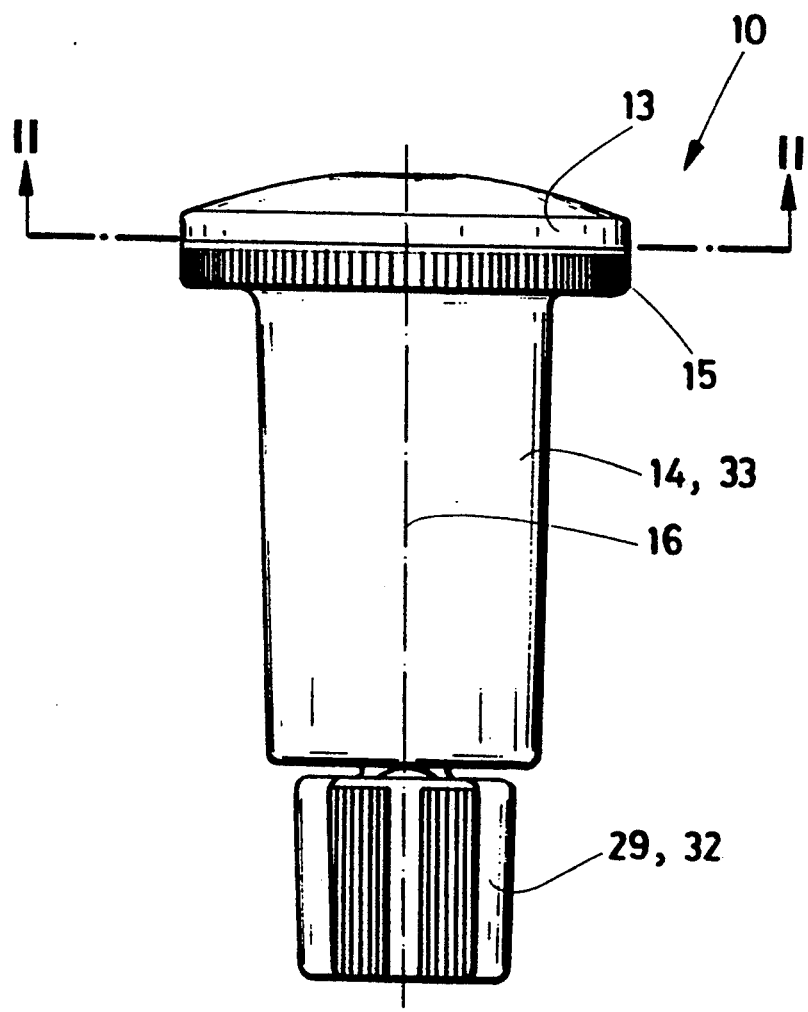
FIG. 1 shows a side view of a lancet device, comprised of an insert and a bushing in their assembled state, in an enlarged representation.

The lancet device of the present invention for puncturing the skin of mammals is primarily characterized by:

A bushing having a grip portion and opposite the grip portion a free end defining a plane;

An insert axially slidably connected within the bushing, the insert having a first and a second end, the first end having a grip element and the second end having a projecting lancet with a tip for puncturing the skin; and The grip element comprising a diaphragm with a preset pressure point, wherein, upon surpassing the pressure point of the diaphragm with an axially directed force in the direction toward the free end of the bushing, the lancet is released via the insert with a preset impulse and penetrates the plane defined by the free end to puncture the skin.

According to the present invention the grip element of the insert is at least partially embodied as a spring-elastic body in the form of a diaphragm which releases the lancet via the insert with a predetermined impulse after surpassing a pressure point determined by the diaphragm by applying an axially directed force in the direction to the free end of the bushing so that the lancet penetrates the plane defined by the free ends of the bushing and punctures the skin.

The advantage of the inventive lancet device lies essentially in the fact that the insert is continuously, i.e., also in its rest position, in which the lancet device does not perform its function, is located in the interior of the bushing and surrounded by the bushing so that an accidental contact of the lancet tip and thus a contamination with microbiological bacteria or viruses or other contaminants is impossible. Furthermore, it is an essential advantage that the actuation of the puncturing process is substantially free of individual characteristics of the operator using the lancet device, i.e., the operator must only apply enough pressure for surpassing the pressure point of the spring-elastic diaphragm and after surpassing the pressure point the spring constant of the diaphragm determines the impulse at which the lancet tip within the insert is released and penetrates the skin of the human to the predetermined depth. Furthermore, it is advantageous that the inventive lancet device can be manufactured in a simple manner as two separate parts which subsequently can be easily assembled. This avoids expensive manufacturing tools and expensive or complicated manufacturing processes.

In a preferred embodiment of the lancet device the diaphragm is a plate-shaped body having a concave cross-section. The outer convex curvature of the diaphragm in the initial state of the lancet device is embodied axially outwardly with respect to the bushing. In general, it is possible to embody the diaphragm in any desired and suitable manner; however, it is advantageous, because the manufacturing cost of the lancet device can be reduced, to embody the diaphragm and the shaft-like insert as a unitary part so that in principle the lancet device is comprised only of the insert with diaphragm and the bushing into which the insert is introduced.

In a further embodiment of the present invention the insert has a shaft with first projections and the bushing has an interior with second projections, whereby the first projections interlock with the second projections upon insertion of the insert into the bushing. After insertion of the insert into the bushing the insert cannot be removed without destroying the two components which is advantageous because both components form an operative unit which can be easily stored and can be easily handled for performing the desired puncturing function.

In another advantageous embodiment of the present invention, the insert further comprises a cover element connected to the second end for enclosing the lancet in a sterile manner. It is, of course, possible to sterilize in a suitable manner the lancet device without this cover element, respectively, the individual parts of the lancet device, after manufacture and to enclose the components in an air-tight envelope so that for using the lancet device only the envelope must be cut open and the lancet device removed. However, it has been proven advantageous for cost considerations as well as for reasons of a simpler handling to simply provide a cover element in the aforedescribed manner so that the lancet tip is covered in a sterile manner and the cover element must be removed from the lancet tip immediately before using the lancet device.

Preferably, the insert and the cover element form a unitary part. This is advantageous because the insert and cover element can be manufactured in one step resulting in a more economical manufacturing process.

In order to be able to remove in a simple and fast manner the cover element from the lancet device for the puncturing step and to thereby free the lancet tip, the cover element has a transition into the second end of the insert, whereby the transition has a designated breakage zone. This designated breakage zone allows for a fast removal of the cover element, especially when the designated breakage zone is advantageously formed by a radial recess within the transition so that the cover element can simply be slightly rotated relative to the insert about its axis to thereby break the connection between the insert and the cover element, i.e., the transition breaks at the recess.

Preferably, the cover element has a segment projecting from the bushing when the shaft with the first projections is interlocked with second projections of the bushing, whereby the segment forms a grip. By providing this grip it is ensured that the removal of the cover element from the insert is possible without actuating the spring-elastic diaphragm, i.e., the removal of the cover element is possible without first activating the lancet device. Preferably, the grip has a substantially oval cross-section.

The grip portion of the bushing is preferably a plate-shaped body supporting the grip element of the insert when the shaft with the first projections is interlocked with the second projections of the bushing. With this embodiment the grip element and the grip portion together form a unit which can be easily handled when compared to the known lancet devices.

In general, the bushing can have a body that is formed in any suitable manner, for example, with a circular cross-section. However, it has been proven advantageous that the body of the bushing have an essentially oval cross-section and that the interior of the body of the bushing also have an oval cross-section. A body of the bushing designed as aforedescribed easily allows for the penetration of the insert with the integral grip preferably having also an oval cross-section, i.e., the grip essentially comprises two wing-like parts which allow for a simple removal of the cover element for freeing the lancet tip.

In general it would be possible to use the lancet device multiple times due to its construction because due to the suitable counter position of the lancet tip on a resistance-providing support the diaphragm, after surpassing its predetermined pressure point, can be displaced into its initial position. This could, for example, be useful when for the same patient, due to the lack of readily accessible blood vessels, not enough blood for blood tests can be drawn in the first attempt.

However, in other embodiments of the lancet device for single use, it is advantageous to provide the insert with first blocking elements and the bushing with second blocking elements whereby the first blocking elements engage the second blocking elements such that a further release of the lancet after the lancet has been used once is impossible.

DESCRIPTION OF PREFERRED EMBODIMENTS

Figure 2:
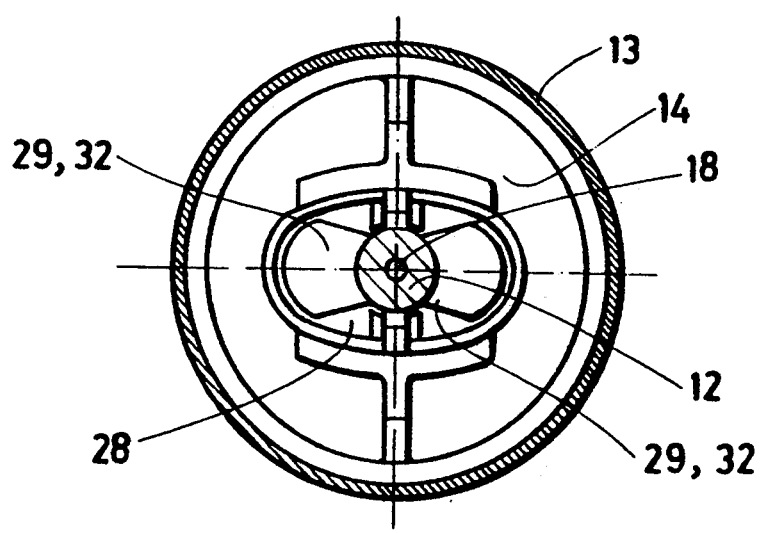
FIG. 2 shows a section along the line II—II of the lancet device represented in FIG. 1.
Figure 6:
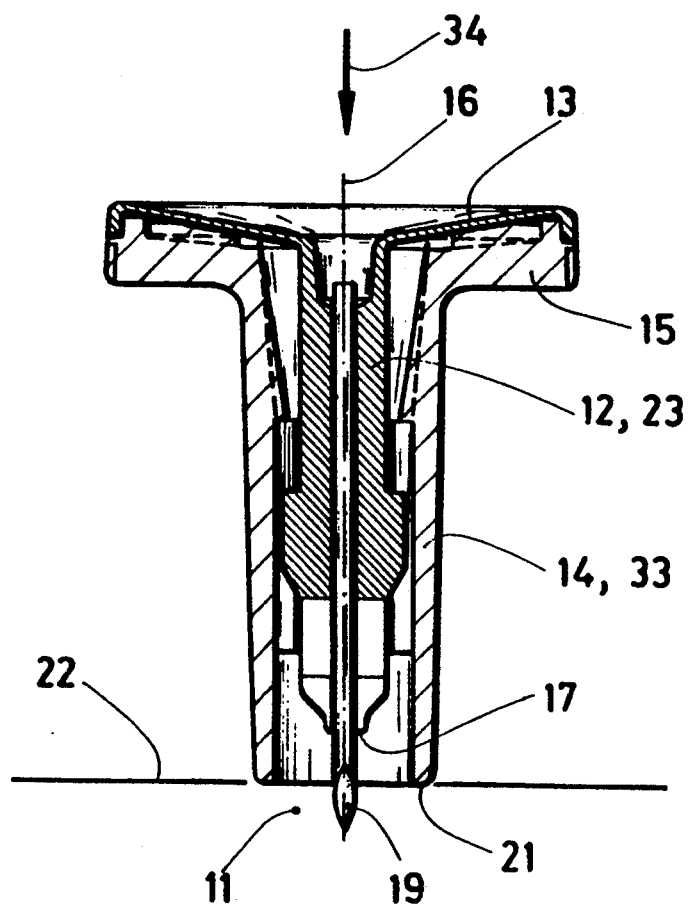
FIG. 6 is a representation according to FIG. 5 in section, with the cover element removed from the lancet tip and with the lancet tip penetrating the skin in a designated puncturing step.

The present invention will now be described in detail with the aid of several specific embodiments utilizing FIGS. 1 through 6.

The lancet device 10 is essentially comprised of an insert 12 and a bushing 14 which in the assembled state together with the lancet 18 form the complete lancet device. The insert 12 has a substantially cylindrical shaft 23 into which the lancet 18 is embedded essentially axially relative to the axis 16 of the insert. The lancet 18 is generally comprised of a biocompatible stainless steel. Furthermore, the insert is provided with radially extending projections 24, 25 at its shaft 23. The projections 24, 25 cooperate with projections 26, 27 that are arranged in the interior 28 of the bushing 14. This will be described in detail in the following. At the free end 17 of the insert 12, see especially FIG. 6, the lancet tip 19 projects from the insert 12 during the designated puncturing function. Before carrying out the puncturing function a cover element 29 which is directly connected to the free end 17 of the insert 12 must be removed. In the embodiment represented in the drawings the cover element 17 and the insert 12 are a unitary part of the lancet device 10. With this cover element 29 the lancet tip is enclosed in a sterile manner.

In contrast to the known lancets of the prior art, the lancet 18 does not have a rotational securing device, for example, in the form of a flattening of certain portions of the lancet 18. In the present invention, for the manufacture of the insert 12 the frictional force resulting after the manufacturing step due to the shrinking of the material used is dimensioned such that after completion of shrinking no rotation of the lancet 18 is possible. This results in a considerably simplified and less expensive solution in comparison to the known lancet devices.

The transition 30 between the insert 12 and the cover element 29, see especially FIGS. 3 and 4, is provided with a designated breakage zone 31 that is formed by a radial recess in the transition 30. The segment of the cover element 29 which in the interlocked state of the bushing 14 and the insert 12 extends past the bushing body 33, compare FIG. 1, forms a grip 32 which in cross-section is oval, respectively, double winged. By rotating the grip 32 relative to the shaft 23 of the insert 12 the designated breakage zone 31, which is formed by the radial recess within the transition 30, is broken and the cover element 29 can be removed from the lancet tip 19.

The grip element 13 of the insert 12 which is formed at the end of the shaft 23 remote from the lancet tip 19 is in the form of a spring-elastic membrane 20. The membrane 20 is an essentially plate-shaped body which in cross-section is concavely curved. In the rest position the highest point of the outer convex curvature of the diaphragm points away from the shaft 23, compare FIGS. 1 to 5. The bushing 14 also comprises a grip portion 15 which is also essentially a plate-shaped body. The grip portion 15 is provided with a peripheral recess which is designed such that the grip element 13 of the insert 12 with its peripheral lateral edge rests within this recess, compare FIGS. 1 and 5. The body 33 of the bushing 14 has an inner and an outer contour of a substantially oval cross-section, i.e., the interior 28 of the bushing 14, see FIG. 2, has also an oval cross-section. As mentioned before, the interior 28 is provided with projections 26, 27 which after insertion of the insert 12, compare FIG. 5, interlock with the projections 24, 25 of the shaft 23 of the insert 12.

For the designated use of the lancet device 10 for performing a puncturing of the human skin 11 the insert 12 is first introduced into the interior 28 of the bushing 14 so that the projections 24, 25 interlock with the projections 26, 27. This step must still be considered a manufacturing step. Due to the elastic prestress of the spring-elastic diaphragm 20 which is essentially formed by the grip element 13, the insert 12 is immobile in the direction of the axis 16. After removal of the cover element 29 from the lancet tip 19, as described before, the lancet tip 19 is freed within the interior 28 of the bushing 14 without at this point penetrating the plane 22 defined by the free end 21 of the bushing 14. When an operator exerts a force in the direction of arrow 34 which is sufficient to overcome the pressure point in the axial direction toward the free end of the bushing 21 (arrow 34), the spring-elastic body (diaphragm 20) applies a predetermined impulse to the insert 12 and thus to the embedded lancet 18 which then penetrates the plane 22 due to this impulse and punctures the skin 21 of a human, compare FIG. 6, to the predetermined depth. The predetermined depth of penetration of the lancet tip 19 into the skin 21 is determined by the constructive embodiment of the axial displacement of the diaphragm 20. The inventively used material is preferably polyethylene, polypropylene, or any other plastic material suitable for injection molding that is furthermore biocompatible and safe with respect to human health.

The present invention is, of course, in no way restricted to the specific disclosure of the specification and drawings, but also encompasses any modifications within the scope of the appended claims.

What we claim is:

1. A lancet device for puncturing the skin of mammals, said lancet device comprising:
   a bushing having a grip portion and opposite said grip portion a free end defining a plane;
   an insert axially slidably connected within said bushing, said insert having a first and a second end, said first end having a grip element and said second end having a projecting lancet with a tip for puncturing the skin; and
   said grip element comprising a diaphragm with a preset pressure point in the form of a spring-elastic body having a concave cross-section, wherein in an initial state of said diaphragm the outer convex curvature is axially outward relative to said bushing and, upon surpassing said pressure point of said diaphragm with an axially directed force in the direction toward said free end of said bushing, said lancet is released via said insert with a preset impulse and penetrates said plane defined by said free end to puncture the skin.

2. A lancet device according to claim 1, wherein said diaphragm is a plate-shaped body having a concave cross-section.

3. A lancet device according to claim 1, wherein said insert and said grip element with said diaphragm form a unitary part.

4. A lancet device according to claim 1, wherein said insert has a shaft with first projections and wherein said bushing has an interior with second projections, with said first projections interlocking with said second projections upon insertion of said insert into said bushing.

5. A lancet device according to claim 4, wherein said insert further comprises a cover element connected to said second end for enclosing said lancet in a sterile manner.

6. A lancet device according to claim 5, wherein said insert and said cover element form a unitary part.

7. A lancet device according to claim 6, wherein said cover element has a transition into said second end of said insert, said transition having a designated breakage zone.

8. A lancet device according to claim 7, wherein said designated breakage zone is a radial recess.

9. A lancet device according to claim 5, wherein said cover element has a segment projecting from said bushing when said shaft with said first projections is interlocked with said second projections of said bushing, said segment forming a grip.

10. A lancet device according to claim 9, wherein said grip has a substantially oval cross-section.

11. A lancet device according to claim 4, wherein said grip portion is a plate-shaped body supporting said grip element of said insert when said shaft with said first projections is interlocked with said second projections of said bushing.

12. A lancet device according to claim 1, wherein said bushing has a substantially oval cross-section.

13. A lancet device according to claim 1, wherein said insert further comprises first blocking elements and said bushing further comprises second blocking elements, said first blocking elements engaging said second blocking elements for blocking a further release of said lancet after said lancet has been used once.

* * * * *